(12) United States Patent
Mir et al.

(10) Patent No.: US 8,227,435 B2
(45) Date of Patent: Jul. 24, 2012

(54) ELECTROTRANSFER OF NUCLEIC ACID INTO TISSUE CELLS

(75) Inventors: Luis Mir, Verriers le Buisson (FR); Damijan Miklavcic, Kranj (SI)

(73) Assignees: Bioalliance Pharma, Paris (FR); Centre National de la Recherche Scientifique (C.N.R.S.), Paris (FR); Institut Gustave Roussy, Villejuif (FR)

( * ) Notice: Subject to any disclaimer, the term of this patent is extended or adjusted under 35 U.S.C. 154(b) by 330 days.

(21) Appl. No.: 11/514,354

(22) Filed: Sep. 1, 2006

(65) Prior Publication Data

US 2008/0027018 A1    Jan. 31, 2008

Related U.S. Application Data

(60) Provisional application No. 60/713,623, filed on Sep. 2, 2005.

(30) Foreign Application Priority Data

Sep. 2, 2005 (EP) .................................. 05291825

(51) Int. Cl.
*A61K 48/00* (2006.01)
(52) U.S. Cl. ........................................ 514/44; 424/93.1
(58) Field of Classification Search .................. 514/44; 424/93.1
See application file for complete search history.

(56) References Cited

U.S. PATENT DOCUMENTS 6,027,488 A * 2/2000 Hofmann et al. ............. 604/522
6,593,130 B1 * 7/2003 Sen et al. ..................... 435/285.2

FOREIGN PATENT DOCUMENTS

| WO | WO-99/01175 | | 1/1999 |
|----|-------------|---|--------|
| WO | WO03009866 | * | 6/2003 |

OTHER PUBLICATIONS

Gazdhar et al, (J Gene Med, 8: 910-918, 2006.*
Voskoglou-Nomikos et al (Clinical Cancer Research, 9, 4227-4239, 2003.*
Kelland et al (European Journal of Cancer, 40: 827-836, 2004.*
Luxembourg et al (Expert Opin Biol Ther, 7(11):1647-1664, 2007.*
Satkauskas et al, "Mechanisms of in vivo DNA electrotransfer: respective contributions of cell electropermeabilization and DNA electrophoresis" Feb. 2002, pp. 133-140, vol. 5, No. 2, Molecular Therapy: The Journal of the American Society of Gene Therapy.
Bureau et al, "Importance of association between permeabilization and elctrophoretic forces for intramuscular DNA electrotransfer" May 1, 2000, pp. 353-359, vol. 1474, No. 3, BBA-General Subjects, Elsevier Science Publishers, Netherlands.
Trochon-Joseph et al, "Evidence of antiangiogenic and antimetastatic activites of the recombinant disintegrin domain of metargidin" Mar. 15, 2004, pp. 2062-2069, vol. 64, No. 6, Cancer Research.
Andre et al, "DNA electrotransfer: Its principles and an updated review of its therapeutic applications." 2004, pp. S33-S42, vol. 11, No. Suppl. 1, Gene Therapy 2004 United Kingdom.
Gothelf et al, "Electrochemotherapy: Results of cancer treatment using enhanced delivery of bleomycin by electroporation" 2003, pp. 371-387, vol. 29, No. 5, Cancer Treatment Reviews 2003 United Kingdom.

* cited by examiner

*Primary Examiner* — Gerald Leffers, Jr.
*Assistant Examiner* — Magdalene Sgagias
(74) *Attorney, Agent, or Firm* — Stephen J. Weyer, Esq.; Stites & Harbison PLLC (57) ABSTRACT

The electrotransfer of a nucleic acid into tissue cells, in particular in a muscle or a tumoral tissue, is carried out by an electric stimulation of the tissue as follows:

first with at least one, preferably a single, pulse of a High Voltage field strength of between 200 and 2000 volts/cm second with a single pulse of Low Voltage field strength of between 50 and 200 volts/cm and of duration of between 300 ms and 2000 ms.

36 Claims, 10 Drawing Sheets

SEQUENCE LISTING

```
<160> NUMBER OF SEQ ID NOS: 2

<210> SEQ ID NO 1
<211> LENGTH: 273
<212> TYPE: DNA
<213> ORGANISM: Homo sapiens
<220> FEATURE:
<221> NAME/KEY: CDS
<222> LOCATION: (1)..(273)

<400> SEQUENCE: 1 atg gct gct ttc tgc gga aat atg ttt gtg gag ccg ggc gag cag tgt      48
Met Ala Ala Phe Cys Gly Asn Met Phe Val Glu Pro Gly Glu Gln Cys
1               5                   10                  15 gac tgt ggc ttc ctg gat gac tgc gtc gat ccc tgc tgt gat tct ttg      96
Asp Cys Gly Phe Leu Asp Asp Cys Val Asp Pro Cys Cys Asp Ser Leu
            20                  25                  30
```

-continued

```
acc tgc cag ctg agg cca ggt gca cag tgt gca tct gac gga ccc tgt    144
Thr Cys Gln Leu Arg Pro Gly Ala Gln Cys Ala Ser Asp Gly Pro Cys
        35                  40                  45 tgt caa aat tgc cag ctg cgc ccg tct ggc tgg cag tgt cgt cct acc    192
Cys Gln Asn Cys Gln Leu Arg Pro Ser Gly Trp Gln Cys Arg Pro Thr
    50                  55                  60 aga ggg gat tgt gac ttg cct gaa ttc tgc cca gga gac agc tcc cag    240
Arg Gly Asp Cys Asp Leu Pro Glu Phe Cys Pro Gly Asp Ser Ser Gln
65                  70                  75                  80 tgt ccc cct gat gtc agc cta ggg gat ggc gag                        273
Cys Pro Pro Asp Val Ser Leu Gly Asp Gly Glu
                85                  90
```

<210> SEQ ID NO 2
<211> LENGTH: 91
<212> TYPE: PRT
<213> ORGANISM: Homo sapiens

<400> SEQUENCE: 2

```
Met Ala Ala Phe Cys Gly Asn Met Phe Val Glu Pro Gly Glu Gln Cys
1               5                   10                  15

Asp Cys Gly Phe Leu Asp Asp Cys Val Asp Pro Cys Cys Asp Ser Leu
                20                  25                  30

Thr Cys Gln Leu Arg Pro Gly Ala Gln Cys Ala Ser Asp Gly Pro Cys
        35                  40                  45

Cys Gln Asn Cys Gln Leu Arg Pro Ser Gly Trp Gln Cys Arg Pro Thr
    50                  55                  60

Arg Gly Asp Cys Asp Leu Pro Glu Phe Cys Pro Gly Asp Ser Ser Gln
65                  70                  75                  80

Cys Pro Pro Asp Val Ser Leu Gly Asp Gly Glu
                85                  90
```

ELECTROTRANSFER OF NUCLEIC ACID INTO TISSUE CELLS

This application claims benefit of U.S. Provisional Application No. 60/713,623, filed Sep. 2, 2005.

The present invention is related to the electrically mediated gene transfer of nucleic acids into tissue cells, in particular muscular or tumoral cells.

Electrically mediated gene transfer, also termed DNA electrotransfer or electrogenetherapy, has gained a real interest as it is one of the most effective methods of in vivo non-viral gene transfer (Andre and Mir, 2004). The method has been shown to be effective to electrotransfer plasmid DNA to various tissues: muscles (Aihara and Miyazaki, 1998; Mir et al., 1998a; Mir et al., 1999), liver (Heller et al., 1996; Suzuki et al., 1998), skin (Titomirov et al., 1991; Zhang et al., 1996), tumors (Heller et al., 2000; Wells et al., 2000; Heller and Coppola, 2002), mouse testis (Muramatsu et al., 1997; Muramatsu et al., 1998), etc (Andre and Mir, 2004).

The mechanisms by which electric pulses mediate DNA transfer into target cells are not well understood. Nevertheless, there is a common agreement that for an improved DNA transfer into tissues, cells in that tissue must be permeabilized. Such a permeabilization can be achieved using simple runs of short square wave electric pulses (in the range of 100 µs) (Mir et al., 1991b; Gehl et al., 1999; Miklavcic et al., 2000). This kind of pulses has been widely used for the local delivery of non-permeant anticancer drugs (like bleomycin or cisplatin) in a treatment termed 'antitumor electrochemotherapy' (Mir et al., 1991a; Glass et al., 1997; Sersa et al., 1998; Mir et al., 1998b; Rodriguez et al., 2002). Indeed, the delivery to tumors of e.g. 8 pulses of 1300 V/cm and 100 µs either in vitro or in vivo is sufficient to induce transient rearrangements of the cell membrane that allow non-permeant anticancer molecules like bleomycin to enter the cell by diffusion and to fully exert their cytotoxic activity (Poddevin et al., 1991; Mir et al., 1991; Gehl et al., 1998).

These short permeabilizing electric pulses have also been shown to increase the transfer of plasmid DNA into several tissues (Heller et al., 1996; Heller et al., 2000). However, another type of square-wave electric pulses was applied to muscles (Aihara and Miyazaki, 1998; Mir et al., 1999), tumors (Rols et al., 1998), liver (Suzuki et al., 1998) and some other tissues (Andre and Mir, 2004), and was found to be more effective for DNA electrotransfer (Mir et al., 1999; Heller et al., 2000). These pulses usually are of lower voltage but much longer duration (in the range of tens of milliseconds) (Aihara and Miyazaki, 1998; Rols et al., 1998; Mir et al., 1999; Bettan et al., 2000; Matsumoto et al., 2001). It is assumed that this type of pulses mediate DNA transfer into the cells by inducing two distinct effects that include cell permeabilization (like the short pulses) and DNA electrophoretic migration during the delivery of the electric field (Klenchin et al., 1991; Sukharev et al., 1992; Neumann et al., 1996; Mir et al., 1999; Golzio et al., 2002).

Efficient electrotransfer into muscle cells has been described in WO-A-99/01158 using one or more (up to 100,000) unipolar electric impulsions of 1-800 volts/cm and in WO-A-98/43702 using stimulation with an electric current of 5-200 volts/cm, wherein the electric current may be in the form of 2-30,000 square bipolar pulses.

The double role of the electric pulses on in vivo DNA electrotransfer was demonstrated by using combinations of electric pulses consisting of high voltage, short pulses (or HV; e.g. 800 V/cm and 100 µs) followed by low voltage, long pulses (or LV; e.g. 80 V/cm and 100 ms) (Bureau et al., 2000; Satkauskas et al., 2002). In this last study it has been shown that these HV and LV pulses can be separated by various lags between the HV and the LV(s) without significant loss in transfection efficiency. These lags ranged up to 300 s for 1HV and 1LV, and up to 3000 s for 1HV and 4LV combinations (Satkauskas et al., 2002).

The applicant has found that it was still possible to improve the electrotransfer efficiency by using a specific combination of HV and LV pulses.

Transfection of tumors and/or other tissues e.g. the liver, can also be of interest for similar purposes. Preferred electric field strength (in V/cm) for the HV and/or the LV will change according to the tissues.

A first object of the invention is thus the use of a nucleic acid for the preparation of a human or veterinary medicament or drug intended to be transferred in vivo into tissue cells, wherein the medicament is brought into contact with tissue cells and the tissue is electrically stimulated as follows:
   first with at least one pulse of a High Voltage (HV) field strength of between 200 and 2000 volts/cm
   second with a single pulse of Low Voltage (LV) field strength of between 50 and 200 volts/cm and of duration of between 300 and 2000 ms.

As used herein, the term "tissue" denotes a tumoral or non tumoral tissue of an animal, for instance a human, or a non human Mammal such as a rodent (e.g. a mouse, a rabbit or a rat), a dog, a cat, or a primate. A non tumoral tissue may be a muscle, especially skeletal muscle, or liver.

According to an embodiment, the tissue is a muscle. For this kind of tissue, but not exclusively, it is preferred that the tissue be electrically stimulated first with at least one pulse of a HV field strength of between 200 and 1400 volts/cm.

According to another embodiment, the tissue is a tumoral tissue. For this kind of tissue, but not exclusively, it is preferred that the tissue be electrically stimulated first with at least one pulse of a HV field strength of between 400 and 2000 volts/cm.

Preferably, the medicament is intended to be brought into contact with the tissue cells before applying the single LV pulse and still more preferably, before the application of the HV pulse or pulses. The time between injection of nucleic acid and electrical pulse, especially between injection and HV pulse or pulses, is not critical. Typically, the medicament has been brought into contact with the tissue cells from few seconds to 10 minutes, e.g. from 30 s and 5 minutes. An interval of 5 to 10 minutes before the HV pulse or pulses is also acceptable. The medicament may be brought into contact through direct intramuscular injection, through systemic administration (e.g. intravenous or intra-arterial route) or by topical or subcutaneous administration.

In an advantageous aspect of the invention, in particular for a muscle, the single LV pulse has a field strength of between 50 and 140 volts/cm, especially of between 80 and 120 volts/cm, preferably of between 90 and 110 volts/cm, typically about 100 volts/cm.

In an advantageous aspect of the invention, in particular for a tumoral tissue, the single LV pulse has a field strength of between 100 and 200 volts/cm, preferably of between 120 and 160 volts/cm, typically about 140 volts/cm.

In another advantageous aspect of the invention, for muscle and tumoral tissue, the single LV pulse has a duration of between 300 and 800 ms, preferably of between 350 and 600 ms, typically about 400 ms.

The LV pulse may be of the same polarity than the HV pulse.

However, according to an advantageous aspect, the LV pulse has a polarity opposed to that of the HV pulse.

Preferably, the single LV pulse is a squared pulse. It can also be trapezoidal, or discontinuous.

Without being bound to theory, it is deemed the single LV pulse according to the invention at least improves the nucleic acid electrophoretic migration.

There can be several HV pulses, i.e. from 2 to 10 HV pulses having the specifications disclosed therein. It is more convenient in this case to have identical HV pulses.

However, it has been demonstrated that a single HV pulse having the specifications disclosed therein is sufficient to permeabilize the cell membrane. Therefore, in the preferred embodiment, use is made of a single HV pulse.

In a further advantageous aspect of the invention, for a muscle but not exclusively, the HV pulse has a field strength of between 300 and 1300, preferably of between 400 and 1200 volts/cm, more preferably of between 500 and 900, still more preferably of between 600 and 800 volts/cm, typically about 700 volts/cm.

In a further advantageous aspect of the invention, for a tumoral tissue but not exclusively, the HV pulse has a field strength of between 600 and 2000, preferably of between 800 and 1600 volts/cm, more preferably of between 900 and 1200, typically about 1000 volts/cm.

In still a further advantageous aspect of the invention, for muscle or tumoral tissue, the HV pulse has a duration of between 10 and 1000 µs, preferably of between 50 and 200 µs, typically about 100 µs.

Where there is a single HV pulse, it is preferably a squared pulse. In case of several HV pulses, use can be made of unipolar or bipolar pulses, or of pulses having different directions and/or polarities, preferably of the squared type.

The HV and LV pulses may be separated by lag and this lag can advantageously be between 300 ms and 3000 s, preferably between 500 ms and 1000 s, typically about 1000 ms.

In a particular embodiment, there is no lag or only a short one, say less than 300 ms, and the HV pulse has a field strength of between 300 and 1000 volts/cm, preferably of between 400 and 800 volts/cm.

The nucleic acid is useful in gene therapy, either through expression of a molecule of interest or through modulation or blocking of a gene within the host that have a therapeutic effect. Preferably, the aims of transfection according to the invention are:
  making the muscle a secretory organ for molecules that have a direct or indirect therapeutic effect, including an immunostimulating or vaccinal effect,
  correcting tissue cell, in particular muscle cell, dysfunction.

In a preferred aspect, the nucleic acid comprises nucleic acid sequences able to express in vivo in the transfected tissue cells one or more therapeutically active molecule(s), preferably a protein or proteins of interest. This active molecule may be therapeutically active by itself or indirectly e.g. through a metabolite of said molecule. It may acts in the tissue itself and/or outside the tissue in another location within the body, for example on a tumour located anywhere in the body if the expressed molecule is active against a tumour. As examples of therapeutic molecules of interest, one may refer to those listed in WO-A-99/01158. It will be appreciated that there is no limitation to the kind of molecules that can be expressed in accordance with the invention and therefore the one skilled in the art will be able to carry out the invention with a molecule of interest knowing the coding sequence thereof and routine experimentation to select the best construction or expression vector.

Any nucleic acid can be used, for example, plasmid DNA, linear DNA, antisense DNA and RNA. In a preferred embodiment, the nucleic acid is a DNA expression vector of the type well known in the art. Generally, an expression vector contains a promoter operably linked to a DNA sequence that codes for the protein of interest, followed by a termination signal such as a polyadenylation signal.

It will be appreciated that the use according to the invention encompasses the case where two or more nucleic acids able to express in vivo different active molecules are used to prepare the medicament. The nucleic acids are preferably chosen so as to be complementary and/or act in a synergistic way in treating a condition.

Also, is encompassed the use of at least one nucleic acid that is able to express in vivo at least two active molecules, that preferably are complementary and/or act in a synergistic way in treating a condition. In that case, the nucleotide sequences encoding the different molecules may be under the control of the same promoter or different promoters.

According to various aspects of the invention the nucleic acid expresses one or several (at least 2) active molecule(s) selected so that:
  the medicament is efficient in reducing, suppressing or regressing tumor angiogenesis,
  the medicament reduces or suppress tumor growth,
  the medicament inhibits metastasis,
  the medicament is against cancer.

One embodiment is to transfect tissue, in particular muscle, cells with a construct comprising the Recombinant human Desintegrin Domain of ADAM-15 gene (RDD gene). This gene, its sequence and useful constructs (e.g. expression vector pBi-RDD) have been fully described in the article by Trochon-Joseph V. et al. 2004 to which the one skilled in the art may refer. The RDD gene and protein sequences are shown in SEQ ID No.1 and SEQ ID NO.2, respectively. RDD may act as an anticancer agent, may reduce or suppress tumor growth, and/or acts as an antiangiogenic and/or antimetastatic agent.

A specific aspect of the invention is thus the use of a nucleic acid encoding the RDD protein or an efficient fragment thereof (efficient means the protein encoded by the fragment elicits the same or a similar therapeutic activity than the whole RDD polypeptide) for the preparation of a medicament intended to be transferred in vivo into tissue cells and to produce therein a RDD polypeptide or a fragment thereof that is therapeutically active, wherein the medicament is injected into a tissue and the tissue is electrically stimulated as follows:
  first with at least one pulse of a High Voltage (HV) field strength of between 200 and 2000 volts/cm
  second with a single pulse of Low Voltage (LV) field strength of between 50 and 200 volts/cm and of duration of between 300 and 2000 ms.

According to an embodiment, the tissue is a muscle. For this kind of tissue, but not exclusively, it is preferred that the tissue be electrically stimulated first with at least one pulse of a HV field strength of between 200 and 1400 volts/cm.

According to another embodiment, the tissue is a tumoral tissue. For this kind of tissue, but not exclusively, it is preferred that the tissue be electrically stimulated first with at least one pulse of a HV field strength of between 400 and 2000 volts/cm.

The various characteristics and aspects described supra, especially in relation with the electrotransfer features and the composition of the nucleic acid, do apply in the same way to this specific use and reference is thus made to the above in this respect in order to further characterize this specific use. This medicament is advantageously useful as an antiangiogenic and/or antimetastatic agent.

In another interesting aspect, as a therapeutically active molecule, the nucleic acid encodes one or several immunogens (or immunogenic peptides, polypeptides or proteins, including glycoproteins) that are able to induce an immune response in the host. In one embodiment, the immune response is a protective immune response for the host. In this embodiment, the invention relates to producing an immunogenic composition or a vaccine or a therapeutic vaccine, that is directed against a microorganism, e.g. virus or bacteria, or against cancers. By way of example only, the nucleic acid encodes one or several (at least 2) immunogens of HIV, HBV, Epstein-Barr virus, pseudorabies virus, syncitia forming virus. The person skilled in the art has access to the nucleic acids encoding the most interesting molecules for the chosen application, for example to the most efficient immunogens or combinations of immunogens for a particular disease.

In another embodiment, the immune response leads to the production of antibodies, especially polyclonal antibodies, and these antibodies are intended to be recovered from the produced serum and used in an usual manner.

An object of the present invention is thus also a method of treatment of a Human or an animal, comprising injecting a nucleic acid into a tissue, and electrically stimulating the tissue as follows:
- first with at least one pulse of a High Voltage (HV) field strength of between 200 and 2000 volts/cm
- second with a single pulse of Low Voltage (LV) field strength of between 50 and 200 volts/cm and of duration of between 300 and 2000 ms, the nucleic acid being transferred into the tissue cells by result of this electric stimulation.

According to an embodiment, the tissue is a muscle. For this kind of tissue, but not exclusively, it is preferred that the tissue be electrically stimulated first with at least one pulse of a HV field strength of between 200 and 1400 volts/cm.

According to another embodiment, the tissue is a tumoral tissue. For this kind of tissue, but not exclusively, it is preferred that the tissue be electrically stimulated first with at least one pulse of a HV field strength of between 400 and 2000 volts/cm.

As described supra, according to a preferred aspect, the nucleic acid is able once transferred in vivo into tissue cells to produce therein a therapeutically active molecule, that is intended to exert directly or indirectly a therapeutic action in the muscle cells and/or at another body location, or still in the tumor tissue cells.

Preferably, as mentioned above, the nucleic acid is injected before applying the single LV pulse and still more preferably, before the application of the HV pulse or pulses.

The various characteristics and aspects described supra in relation with the use according to the invention do apply in the same way to the method of treatment and reference is thus made to the above in order to further characterize this method.

One aspect is thus such a method wherein the nucleic acid encodes the RDD gene or an efficient fragment thereof, as disclosed therein, and the method is intended to reduce or suppress tumor growth, and/or acts as an antiangiogenic and/or antimetastatic agent.

Another aspect is thus such a method wherein the nucleic acid encodes an immunogen, as disclosed therein, and the method is intended to immunize a Human or an animal, or to produce antibodies to be recovered.

Still another object of the invention is the electroporation method itself, comprising placing electrodes near a tissue containing a nucleic acid interstitially, then electrically stimulating the tissue as follows:
- first with at least one pulse of a High Voltage (HV) field strength of between 200 and 2000 volts/cm
- second with a single pulse of Low Voltage (LV) field strength of between 50 and 200 volts/cm and of duration of between 300 and 2000 ms, the nucleic acid being transferred into the tissue cells by result of this electric stimulation.

According to an embodiment, the tissue is a muscle. For this kind of tissue, but not exclusively, it is preferred that the tissue be electrically stimulated first with at least one pulse of a HV field strength of between 200 and 1400 volts/cm.

According to another embodiment, the tissue is a tumoral tissue. For this kind of tissue, but not exclusively, it is preferred that the tissue be electrically stimulated first with at least one pulse of a HV field strength of between 400 and 2000 volts/cm.

The nucleic acid is heterogeneous to the body and is of the type described supra. It is preferably a nucleic acid comprising nucleic acid sequences able to express in vivo in the transfected muscle cells or tumoral tissue one or more therapeutically active molecule(s), preferably a protein or proteins of interest.

In an aspect, the electrodes are placed at the contact of the skin, i.e. outside the body and this does not need any surgery act.

In another aspect, the electrodes are placed at the contact of the tissue, in particular the muscle or tumoral tissue, itself. In that case, the electrodes may be carried by a device making both the injection of the nucleic acid and the electric stimulation. The electrodes may also be separate from the injection device.

The electrodes are to be positioned near the injection site such that electrical current traveling through the electrodes passes through the injection site or region wherein the injected liquid has diffused upon injection.

The various characteristics and aspects described supra, especially in relation with the electrotransfer characteristics and the composition of the nucleic acid do apply in the same way to the electroporation method and reference is thus made to the above in order to further characterize this method.

The invention may also be defined as the use of a nucleic acid which is capable of expressing a molecule in the manufacture of a medicament or drug for use in a method of delivering said nucleic acid to tissue cells, especially tumoral or non tumoral tissue cells, e.g. muscle cells, wherein
a) said nucleic acid is to be injected into the tissue
b) the tissue is electrically stimulated as follows:
- first with at least one pulse of a High Voltage (HV) field strength of between 200 and 2000 volts/cm
- second with a single pulse of Low Voltage (LV) field strength of between 50 and 200 volts/cm and of duration of between 300 and 2000 ms.

As it comes from above, the use may be:
- for immunizing the host by transfecting the nucleic acid in muscle cells, especially skeletal muscle cells of the host, wherein the nucleic acid encodes an immunogen that will induce an immune response in the host
- or for systemically delivering a therapeutically active molecule in the host, by transfecting the nucleic acid in muscle cells, especially skeletal muscle cells or in tumoral tissue cells.

This use may be further defined with the various features defined above concerning especially the conditions of electrostimulation, of administration of the nucleic acid, the composition of the nucleic acid, the nature of the hosts . . . .

Still another object of the invention is a method for the production of antibodies, especially polyclonal antibodies, comprising injecting an immunogen encoding nucleic acid into a tissue, especially a muscle, of a living animal and electrically stimulating the tissue as follows:
- first with at least one pulse of a High Voltage (HV) field strength of between 200 and 2000 volts/cm
- second with a single pulse of Low Voltage (LV) field strength of between 50 and 140 volts/cm and of duration of between 300 and 2000 ms, the nucleic acid being transferred into the tissue cells by result of this electric stimulation and expressing in said host an immunogen able to elicit an immune response in the host, and recovering the antibodies.

The animal may be a mice, a rat or a rabbit or any other animal especially rodent usually used for the production of antibodies.

Recovery of serum and antibodies, purifying and/or concentration of the antibodies may be done using the conventional methods known from the person killed in the art.

This method may be further defined with the various features defined above concerning especially the conditions of electrostimulation, of administration of the nucleic acid, the composition of the nucleic acid, the nature of the hosts . . . .

The present invention will now be described in further details with the presentation of the following non-limitative experiments and with reference to the drawings in which.

EXEMPLE 1

Materials and Methods

Plasmid DNA

The plasmid pXL 3031 (pCMV-Luc+) containing the cytomegalovirus promoter (nucleotides 229-890 of pcDNA3, Invitrogen) inserted upstream of the coding sequence of the modified cytosolic luc+ gene coding for the firefly luciferase (Soubrier et al., 1999) was used. The plasmid DNA was prepared using usual procedures (Ausubel et al., 1994). Alternatively, the pEGFP-N1 plasmid (BD Biosciences Clontech, Saint Quentin Yvelines, France) featuring the gene of the Green Fluorescent Protein (GFP) under the control of the CMV promoter and prepared in PBS (phosphate buffered saline, Gibco, Cergy-Pontoise, France) using the EndoFree Plasmid Giga Kit (QIAGEN, Courtabeuf, France) was also used.

Animals

For all experimental procedures female, 7-9 weeks old, C57Bl/6 mice were anesthetized by the intraperitoneal administration of the anesthetics Ketamine (100 mg/kg; Ketalar, Panpharma, France) and Xylazine (40 mg/kg; Rompun, Bayer, France). Prior to the experiments the legs were shaved using an electric shaver. At least 10 muscles (5 mice) were included in each experimental group for luciferase determinations. In the case of the GFP qualitative data, four muscles were used for each experimental condition.

DNA Injection

For the luciferase experiments, 3 μg of plasmid DNA prepared in 30 μl of 0.9% NaCl were injected. In most of the experiments (FIGS. 1 to 5), the DNA solution was supplemented with 120 IU/ml heparin (Laboratoires Leo, Saint Quentin en Yvelines, France; one mg of the heparin (MW 10-12 kDa) corresponded to approximately 137 IU). The DNA was injected into tibial cranial muscles using a Hamilton syringe with a 26-gauge needle. For GFP experiments, 4 μg in 20 μl of PBS were injected in each treated tibialis, always in the absence of heparin.

DNA Electrotransfer

HV and LV pulse combinations were generated by a device consisting of square wave electropulsator PS-15 (Jouan, St Herblain, France) for the HV and a microprocessor-driven switch/function generator built at the University of Ljubljana, Faculty of Electrical Engineering, Slovenia, for the LV. The device allowed for precise control of every electrical parameter in HV+LV combinations of pulses (Satkauskas et al., 2002).

HV and LV pulse combinations were delivered soon (40±15 s) after intramuscular DNA injection. In all the experiments the lag between HV and LV was fixed to 1 s. For pulse delivery to the muscles stainless plate electrodes 4.4 mm apart were used. The 1-cm plates encompassed the whole leg of the mice. To ensure good contact between the tibial cranial muscle of exposed leg and the plates of the electrodes a conductive gel was used. Electric field values (in V/cm) are always expressed in terms of the ratio of the voltage applied (V) to the distance between the electrodes (cm).

For the GFP experiments the pulses combinations were delivered using a CLINIPORATOR™ (IGEA, s. r. l., Carpi (MO), Italy) generator and 5 mm apart electrodes from the same company.

Luciferase Activity Measurement

The mice were sacrificed 2 days after DNA electrotransfer. The muscles (net weight approximately 60 mg) were took off and homogenized in 1 ml Cell Culture Lysis reagent solution (10 ml Cell Culture Lysis reagent (Promega Charbonnières, France), diluted with 40 ml distilled water and supplemented with 1 tablet of the Protease inhibitor cocktail from Boehringer Mannheim, Mannheim, Germany). After centrifugation at 12,000 rpm for 10 min at 4° C., the luciferase activity was assessed on 10 µl of the supernatant, using a Walac Victor$^2$ luminometer, by integration of the light produced during 1 s, starting after the addition of 50 µl of Luciferase Assay Substrate (Promega) to the muscle lysate. The results were collected from the luminometer in relative light units (RLU). Calibration with purified firefly luciferase protein showed that $10^6$ of RLU correspond to approximately 70 ng of expressed luciferase. The final results were expressed as pg of luciferase per muscle.

GFP Fluorescence Observations

The mice were sacrificed 3 days after the injection of the pEGFP-N1 plasmid and the transfected tissue was observed using a Leica MZ12 fluorescence stereomicroscope with a Leica GFP Plus filter set (Art. No. 10446143: excitation filter 480/40 nm, dichroic mirror 505 nm LP, barrier filter 510 nm LP) (Leica, Rueil-Malmaison, France). Pictures were taken using a digital cooled color camera (AxioCam HRc, Zeiss, Le Pecq, France), and the quantification of the GFP expression was made by software (AxioVision Light Edition Release 4.1.1.0) integration of the light detected by the camera.

Statistical Analysis

For statistical comparison of several groups use was made of two-tailed Student's t-test for unpaired values. In the figures luciferase expression data was reported as mean±SD.

Results

In the case of the luciferase experiments, due to high sensitivity of the measurements, a solution of plasmid DNA supplemented with low amounts of heparin (120 IU/ml) was injected. Heparin at this dose causes a large decrease in the spontaneous uptake of DNA by the muscle but does not significantly impair the efficacy of DNA electrotransfer into the muscle fibers (Satkauskas et al., 2001). Therefore, the respective contributions of HV and LV pulses on the efficiency of DNA electrotransfer can be analyzed more precisely in the presence of heparin. Additionally, the lag between HV and LV pulse(s) was fixed to 1 s.

Influence of HV Pulse Duration and Number

To analyze the role of the electropermeabilizing (HV) pulses the LV pulses giving the best level of gene expression according to previous data (Satkauskas et al., 2002) were used. In accordance with this teaching, the LV component parameters were fixed for this experiment to four LVs of 80 V/cm and 100 ms duration, with a delay between the pulses of 1 second.

Figure 1:
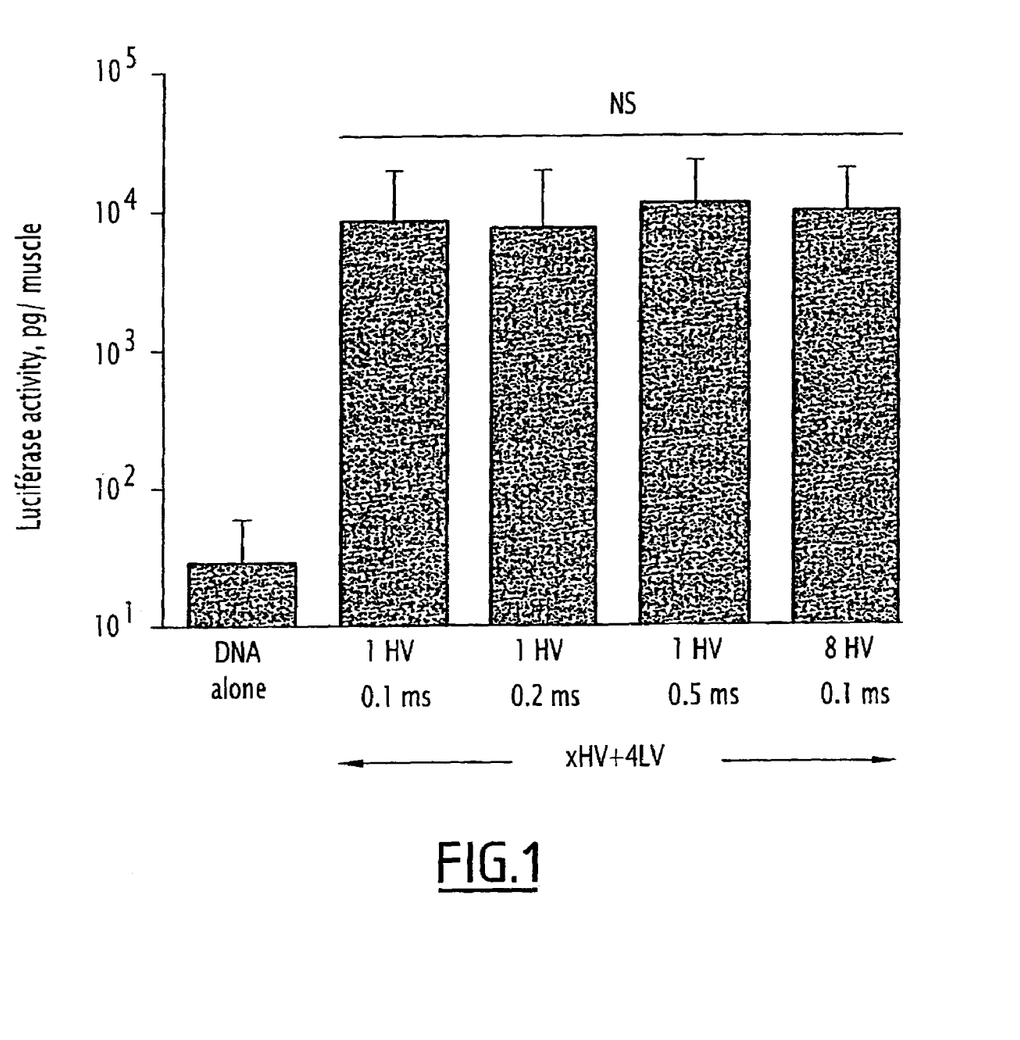
FIG. 1. Luciferase expression after DNA electrotransfer using combinations of one or eight HV pulses (800 V/cm; 0.1, 0.2 or 0.5 ms) and four LV pulses (80 V/cm; 100 ms) (xHV+4LV pulse combination). Data are presented as mean±SD. Statistical difference between each of the xHV+4LV groups was calculated using t-tests; NS—not significant.

Improvement of muscle permeabilization was tried through the increase of either the number of HV pulses (from 1 to 8) or the duration of the HV (from 100 µs to 500 µs). As shown in FIG. 1, neither the increase of HV duration, nor the increase of HV number significantly enhanced muscle transfection.

Figure 2:
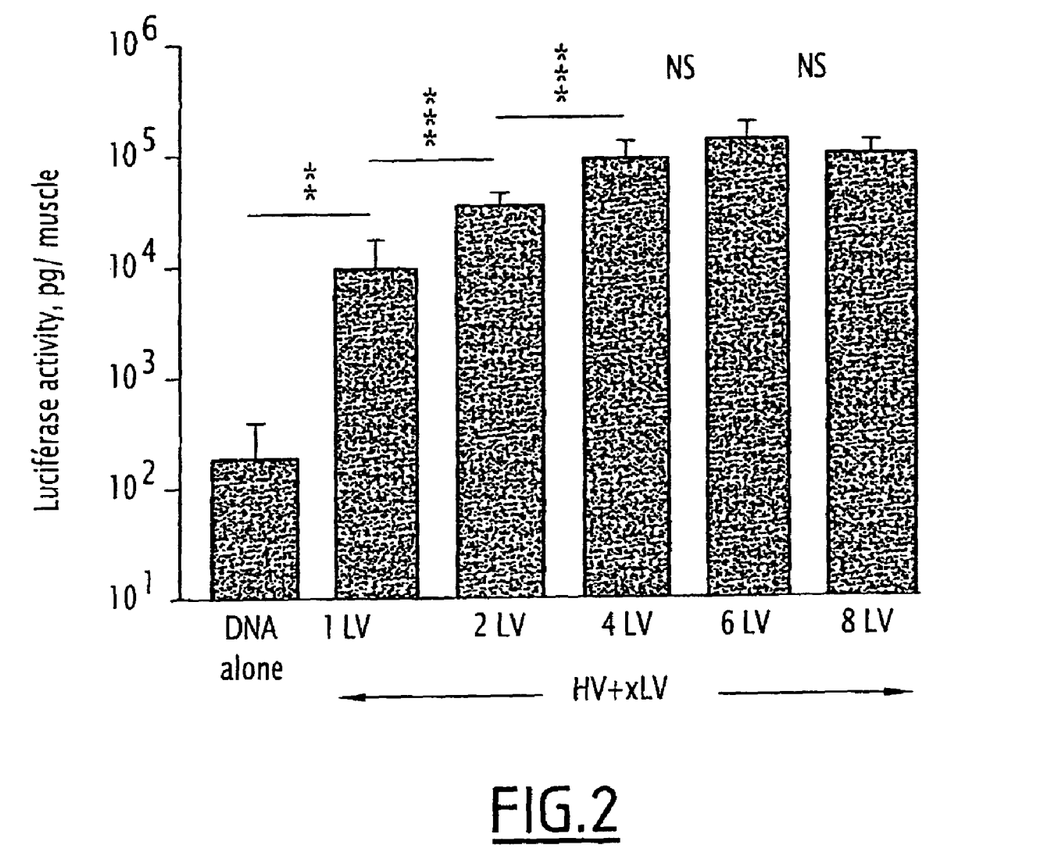
FIG. 2. Luciferase expression after DNA electrotransfer using combination of one HV pulse (800 V/cm; 100 μs) and various number of LV pulses (100 ms; 80 V/cm) (HV+xLV pulse combinations). Data are presented as mean±SD. Statistical difference between neighbor groups shown in the figure was calculated using t-tests and is indicated by asterisks (P<0.01; *P<0.001; NS—not significant).

Influence of LV pulse number As a consequence of the results shown in FIG. 1, one single HV of 800 V/cm and 100 µs was always used to analyze the role of the LV component. First, the influence of the number of LVs was examined. The LV pulse strength was fixed to 80 V/cm, duration to 100 ms and the delay between LVs to 1 s. Luciferase expression markedly increased when LV number was increased from 1 to 4 (FIG. 2). Consistently with previous data (Satkauskas et al., 2002), with four LVs the luciferase expression was 10 times higher than with one LV. No further significant increase was observed with a larger number (6 or 8) of LV pulses (FIG. 2).

Figure 3:
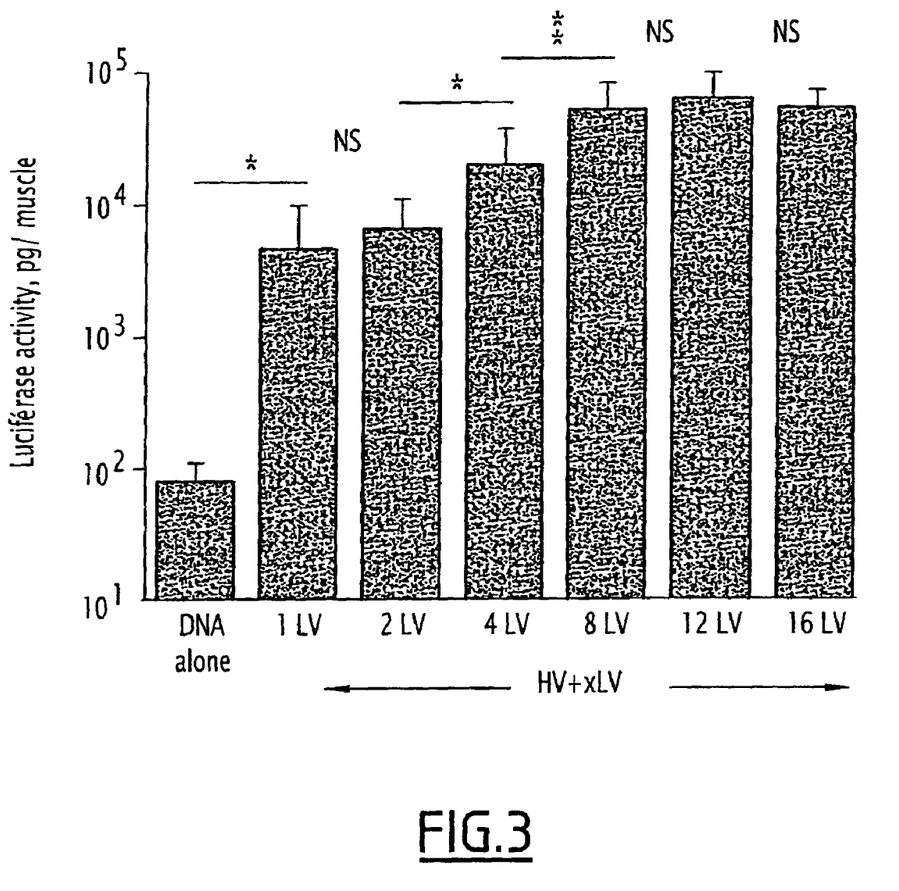
FIG. 3. Luciferase expression after DNA electrotransfer using combination of one HV pulse (800 V/cm; 100 μs) and various number of LV pulses (50 ms; 80 V/cm) (HV+xLV pulse combinations). Data are presented as mean±SD. Statistical difference between neighbor groups shown in the figure was calculated using t-tests and is indicated by asterisks (*P<0.05; **P<0.01; NS—not significant).

Subsequent experiments on the influence of pulse number on gene transfer efficacy were performed using LV(s) of 50 ms duration (FIG. 3). The same trend as in the case of the LV(s) of 100 ms duration (FIG. 2) was observed. In both cases the beginning of the plateau in luciferase gene expression started at a total pulse duration of 400 ms. Again, no further significant increase was observed with increased number (12 or 16) of LV pulses.

Figure 4:
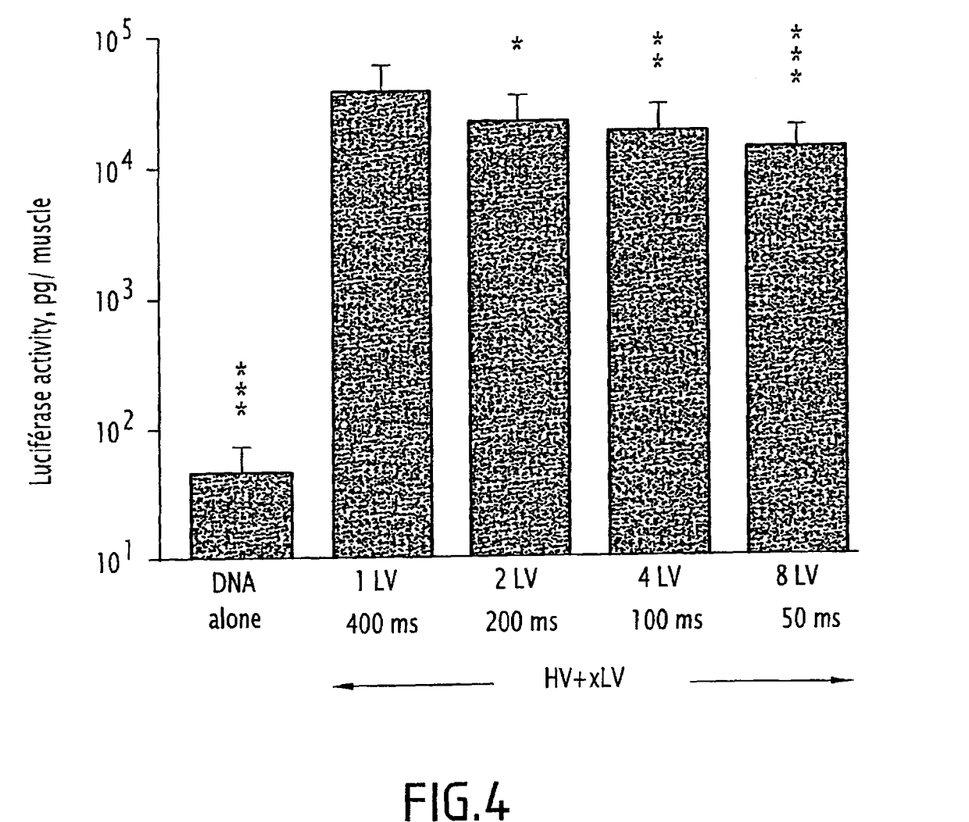
FIG. 4. Luciferase expression after DNA electrotransfer using combination of one HV pulse (800 V/cm; 100 μs) and LV pulse(s) as a function of pulse number and pulse duration of LV pulse(s) keeping constant the total duration of the LV. Data are presented as mean±SD. Statistical difference between the 1HV+1LV (400 ms) group and each of the other groups was calculated using t-tests and is indicated by asterisks (*P<0.05; P<0.01; *P<0.001).

Four different combinations of number and duration of the LVs were further used and compared, all of them resulting in a total duration of the low voltage pulses equal to 400 ms (FIG. 4). A tendency to a progressive decrease in luciferase gene expression with the concomitant decrease in individual pulse duration and increase in pulse number was found (FIG. 4). Remarquably and unexpectedly, HV and LV combinations using a single LV of 400 ms resulted a further increase of and to the best luciferase gene expression, for example about 2 times higher than using eight LVs of 50 ms ($p<0.001$).

GFP Fluorescence Observations

After the electrotransfer of the GFP gene using one HV of 100 µs and 800 V/cm followed after 1 sec delay by one 400 ms LV pulse of either 60, 80 or 100 V/cm, the distribution and the intensity of the fluorescence within the muscles were qualitatively and semi-quantitatively measured using a fluorescence stereo microscope. Pictures were taken either at a constant exposure time (100 ms, Panels A, B and C) or at a variable exposure time, i.e. allowing the camera to adjust the exposure time to acquire an equivalent amount of light from picture to picture (Panels D, E and F). The pictures that have been made represent the images observed in four muscles for each experimental condition. Two series of pictures ere made showing the reproducibility of the results as well as the large increase in fluorescence with the increase in the field strength of the LV pulses (Panels A, B and C). The quantitative analysis of the mean density of the green color in these images sustain the qualitative data: in a relative scale with 256 levels of intensity, the levels 41 (left muscle) and 33 (right muscle) were reached at 60 V/cm (panel A), while levels 111 and 89 were reached at 80 V/cm (panel B) and 138 and 127 at 100 V/cm (panel C). These pictures have also shown that the fluorescent 'optical surface' is identical whatever the LV field strength (Panels D, E and F). This increase in fluorescence results from a larger fluorescence of each fiber, but the volume of tissue affected by the electrotransfer was the same. The increase in the number of plasmid molecules electrotransferred into the fibers explains the observed increase in the fluorescence of the individual fibers.

EXEMPLE 2

The expression vectors used in this experiment were prepared in accordance with Trochon-Joseph V. et al. 2004.

20 µg each of pBi (control), or pBi-RDD (experimental treatment), together with 10 µg of the Tet-tTS and 20 µg of the Tet-On plasmids, in sterile 0.9% NaCl (final volume, 30 µl) were injected into Tibialis cranialis muscles. Two legs per animal underwent electrotransfer.

Electrotransfer was conducted as described below.

Legs of C57BL/6 mice were shaved using an electric shaver on the day before electrotransfer. Before the electrotransfer procedure, animals were anesthetized via the intraperitoneal injection of a mixture of ketamine (100 mg/kg body weight) and xylazine (40 mg/kg).

Plasmid mixture was injected using a Hamilton syringe. A conductive gel was applied to ensure good contact between the leg skin and the two stainless steel plate electrodes (space between the electrodes: 5 mm). Subsequently, one transcutaneous square-wave electric HV pulse of 700V/cm and 100 µs (1 Hz) was first applied to permeabilize membrane. After a 1000 ms pause and without moving electrodes, one transcutaneous square-wave electric LV pulse of 100V/cm and 400 ms was applied to allow DNA entry into cells by electrophoretic migration. Electrotransfer was performed with the electropulsator Cliniporator (IGEA, Italy). The same procedure was followed for each animal group and each leg. 10 mice were used in each group.

Production of RDD from electrotransferred muscles was induced by adding doxycycline into animal drinking water 3 days before tumor implantation. Doxycycline induction was maintained during the experiment.

Log-phase cultured B16F10 melanoma cells were detached with 0.02% EDTA and resuspended to the final concentration of $4 \times 10^6$/ml in sterile 0.9% NaCl. 100 µl of the suspension were injected I.V. into the retro-orbital sinus of mice. Seven days later cell injection, mice were sacrificed, the lungs were excised, and metastatic nodules were counted under a dissecting microscope.

Figure 5:
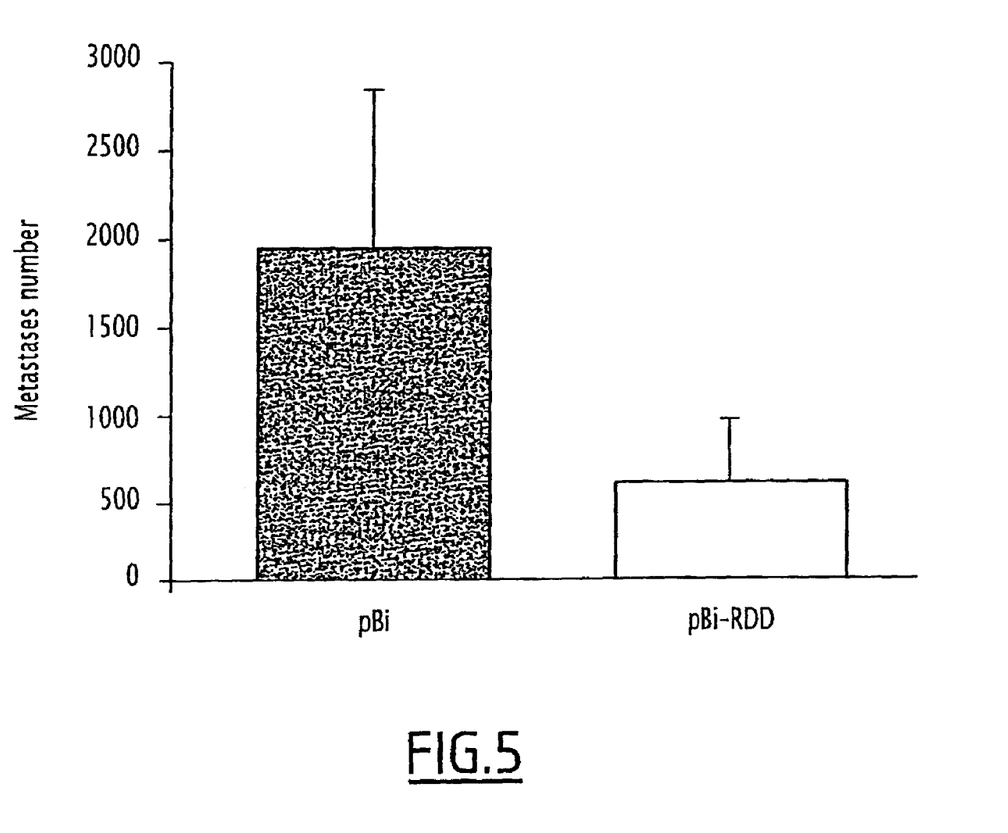
FIG. 5. Metastases number in the mice after electrotransfer of pBi (control) or pBi-RDD.

As shown in FIG. 5, in presence of RDD, 70.5% fewer metastatic nodules were detected in the experimental group than in controls. RDD inhibited the development of B16F10 melanoma.

EXEMPLE 3

Figure 6:
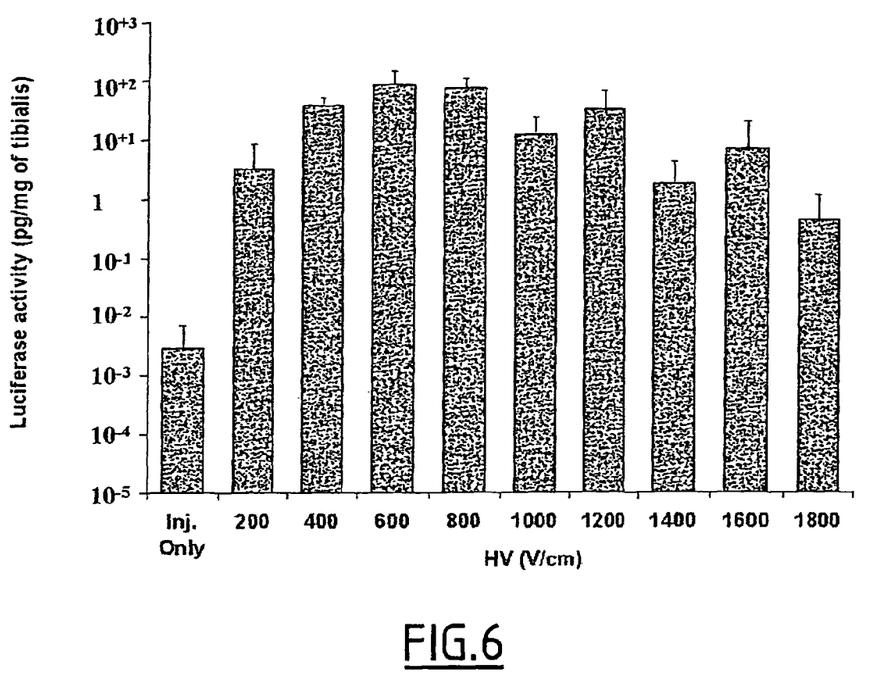
FIG. 6. Luciferase expression after DNA electrotransfer into muscle tibialis using combinations of different HV pulses (200 to 1800 V/cm, 100 μs) followed by one LV pulse (80 V/cm; 400 ms) 1 s after the HV. Data are presented as mean±SD.
Figure 7:
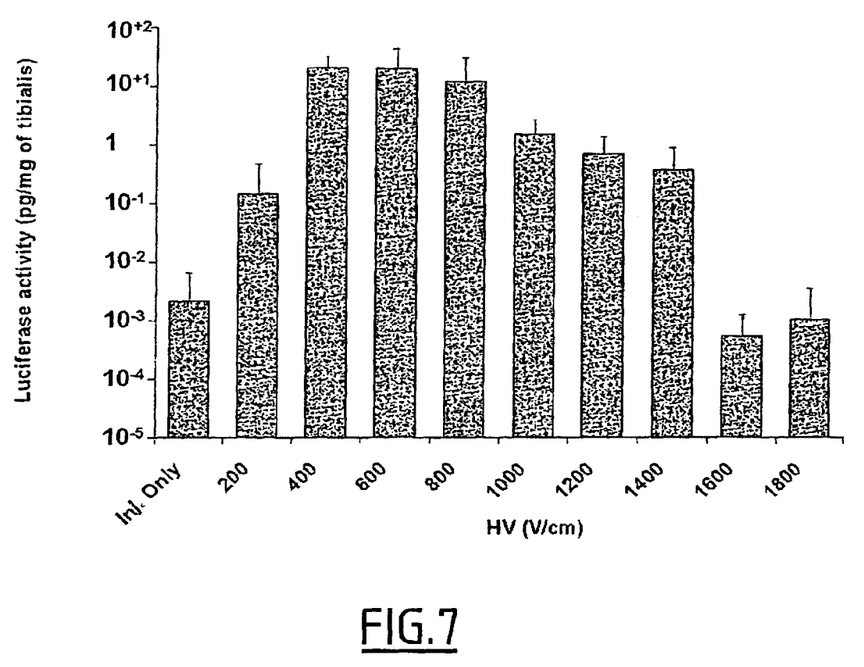
FIG. 7. Luciferase expression after DNA electrotransfer into muscle tibialis using combinations of different HV pulses (200 to 1800 V/cm, 100 μs) followed by one LV pulse (80 V/cm; 400 ms) immediately after the HV. Data are presented as mean±SD.

FIGS. 6 and 7 present the Luciferase expression after DNA electrotransfer into mice muscle tibialis using combinations of different HV pulses (200 to 1800 V/cm, 100 µs) followed by one LV pulse (80 V/cm; 400 ms) 1 s after the HV (FIG. 6) or immediately after the HV (FIG. 7). These experiments have been conducted as in example 1 or the luciferase protocol, on 6 mice for each group, using the CLINIPORATOR™ to deliver the impulsions and the luciferase activity has been expressed in pg/mg of muscle.

EXEMPLE 4

Tumor experiments: B16 F10 melanoma cells were cultured in vitro using classical procedures and MEM culture medium supplemented with 100 U/ml penicillin, 100 mg/ml streptomycin, and 8% foetal calf serum. Young (6-8 weeks) C57Bl/6 female mice were inoculated subcutaneously in the left flank with $1 \times 10^6$ syngenic B16 cells (in 100 µl of MEM culture medium). The tumours were treated when they reached an average diameter of 6-7 mm (7-8 days after inoculation).

50 µg of DNA (plasmid pCMV-Luc+) in 50 µl was locally injected in the tumors using a RN type Hamilton syringe with type 4, 26-gauge, 16 mm length needles. Injection was performed in 15 to 25 seconds Two external stainless steel plate electrodes 1 cm width, 1 mm thickness, and 5 mm apart (IGEA, Carpi, Italy) were placed on the skin at each side of the tumor in order to encompass the whole tumor. The electrical contact was ensured by means of ultrasonography conductive gel (EKO-GEL, Egna, Italy).

Figure 8:
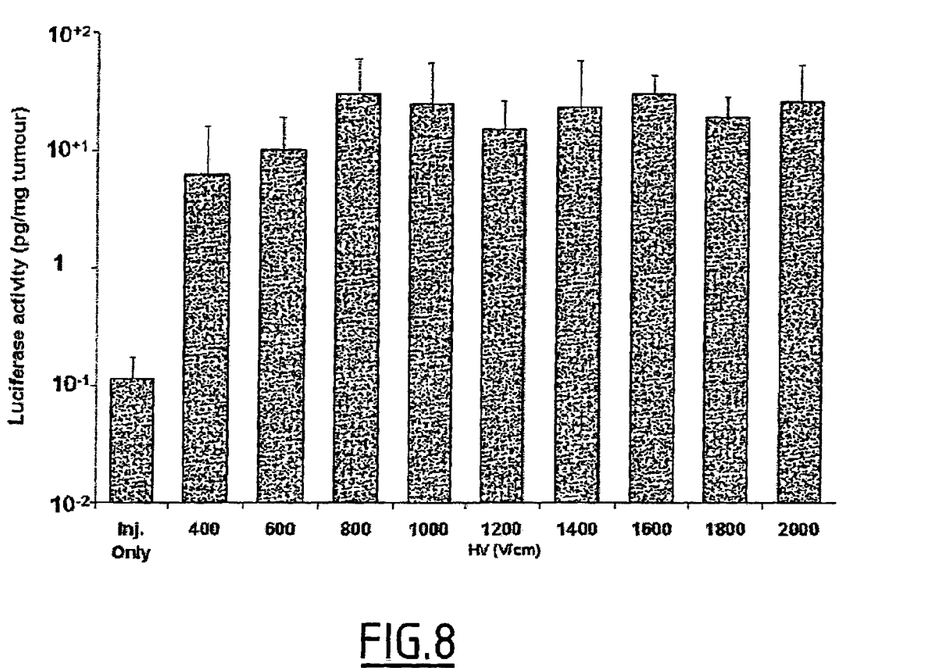
FIG. 8. Luciferase expression after DNA electrotransfer into tumour using combinations of different HV pulses (400 to 2000 V/cm, 100 μs) followed by one LV pulse (80 V/cm; 400 ms). Data are presented as mean±SD.
Figure 9:
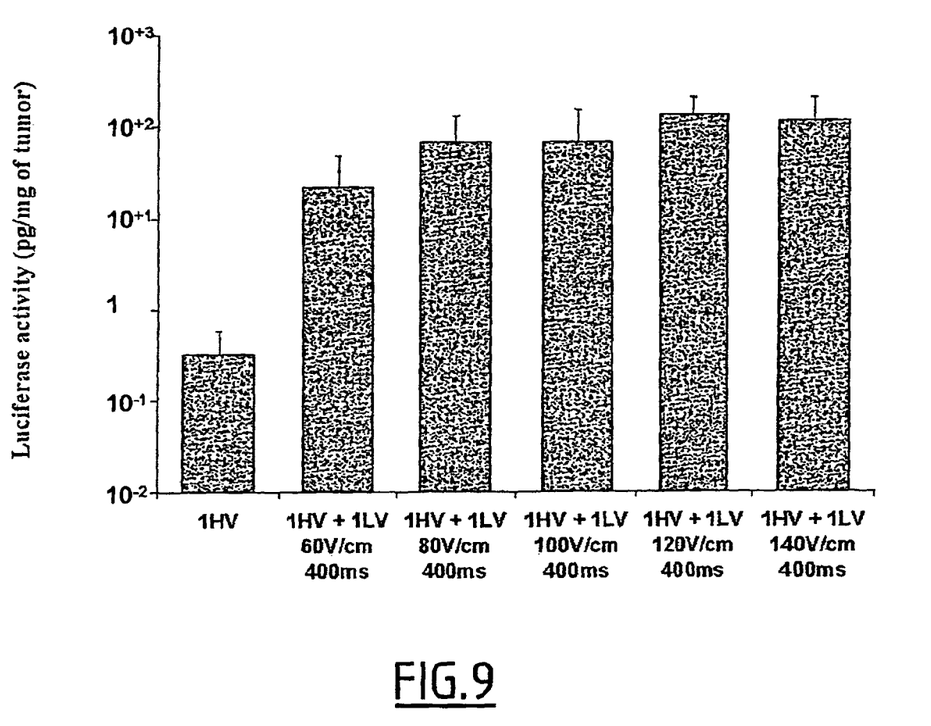
FIG. 9. Luciferase expression after DNA electrotransfer into tumour using combinations of one HV pulse (800 V/cm, 100 μs) followed or not by one LV pulse (at 60, 80, 100, 120 or 140 V/cm; 400 ms). Data are presented as mean±SD.

When a fixed LV component was used (1 LV of 400 ms at 140 V/cm), the results obtained as a function of the HV field strength were similar to those achieved on the skeletal muscle, except that higher field strengths had to be applied to reach the plateau of optimal expression. See FIG. 8.

When a fixed HV component was used (1 HV of 100 µs at 800 V/cm), the results obtained as a function of the LV field strength were similar to those achieved on the skeletal muscle, except that, again, higher field strengths had to be applied to reach the plateau of optimal expression.

The maximal efficacy of the optimal HV+LV pulses was found 10 times higher than the efficacy of trains of identical pulses at previously published optimal conditions (trains of identical square wave pulses).

EXEMPLE 5

Production of Polyclonal Antibodies

—Materials and Methods
Plasmid DNA

The human RDD gene under the control of the murine urokinase secretion signal was inserted into the pVAX1 plasmid (Invitrogen, V260-20) containing the cytomegalovirus (CMV) promoter and the bovine growth hormone polyadenylation signal, to generate the pVAX-RDD plasmid. The empty vector pVAX1 was used as a negative control. Plasmids were prepared in sterile 0.9% NaCl using the EndoFree NucleoSpin Plasmid Kit (Macherey Nagel)
Animals Female Wistar rats were anesthetized by the intraperitoneal administration of the anesthetics Ketamine (40 mg/kg) and Xylazine (5.5 mg/kg). Female New Zealand rabbits were first treated with subcutaneous injection of Calmivet (1 ml/kg) and then anesthetized by intravenous injection of pentobarbital. Prior to the experiments, the legs were shaved using an electric shaver.
DNA Injection and Electrotransfer Penetrating needle electrodes were introduced into the Gracilis muscles for the rabbits and into the Gluteus muscles for the rats. 100 µg of each plasmid DNA prepared in 100 µl of 0.9% NaCl were injected in three times between the electrode lines. Immediately after intramuscular DNA injection, muscle electrotransfer with the CLINIPORATOR™ was performed as previously described: one electric pulse of 700V/cm and 100 µs (1 Hz), a 1000 ms pause and, without moving electrodes, one electric pulse of 100V/cm and 400 ms. The procedure was performed for both legs of each animal, and twice per muscle for rabbits (i.e. 4 injections per animal) and once per muscle for rats (i.e. 2 injections per animal). Animals were immunized at 0, 6, and 12 week.
Measurement of Antibody Reponses Blood were collected before the first immunization, and then at week 4, 9 (sacrifice time for the rabbits), and 16 (sacrifice time for the rats). Serum was recovered by centrifugation. Anti-RDD antibodies (IgG) were measured by ELISA as follows. Each well of 96-well micro-titer plates (Nunc Maxisorb, Roskilde, Denmark) were coated with 100 ng of recombinant RDD produced in *E. coli*. After overnight incubation at 4° C., the wells were washed six times with TBST (Tris-buffered saline TBS, 0.02% Tween 20) and then incubated with TBST-5% milk for 3 h at room temperature under shaking conditions. Once washed, as described above, wells were incubated with 100 µl of serial dilutions of sera in TBST-5% milk (1:125 to 1:8000). An anti-RDD rabbit polyclonal serum produced by peptide immunization (Neosystem) was used as a positive control. After a 2 h incubation with shaking, wells were washed and incubated for 1 h with 100 µl of peroxidase conjugated antibodies diluted to 1:5000 in TBST-5% milk: bound rabbit antibodies were detected with a peroxidase-conjugated anti-rabbit IgG (ref. NA934, Amersham), and bound rat antibodies were detected with a goat F(ab')2 fragment rat IgG (H+L) peroxidase (ref. IM0825, Beckman Immunotech). After washing, as described above, wells were incubated with 200 μl of the substrate o-phenylenediamine dihydrochloride (Sigma Fast OPD peroxidase substrate tablet set) for 30 min. The reaction was stopped by adding 50 μl of 3N HCL, and a spectrophotometric reading was obtained at 490 nm.

The anti-RDD rabbit polyclonal serum used as a positive control was produces according to standard peptide immunization (production performed by Neosystem SA, Strasbourg, France). The selected peptide comprised amino acid residues 57 to 68 from the RDD sequence (SEQ ID NO.2) conjugated to Gluta-KLH (keyhole limpet hemocyanin, a carrier protein to enhance the immunogenicity of small peptides). 2 mg of this peptide were subcutaneously injected to rabbits at week 0, 2, 4 and 8. Blood were collected before the first injection, and then at week 6, 10, and 12, (sacrifice time). Serum collected at week 12 was used as the positive control.

—Results

Figure 10:
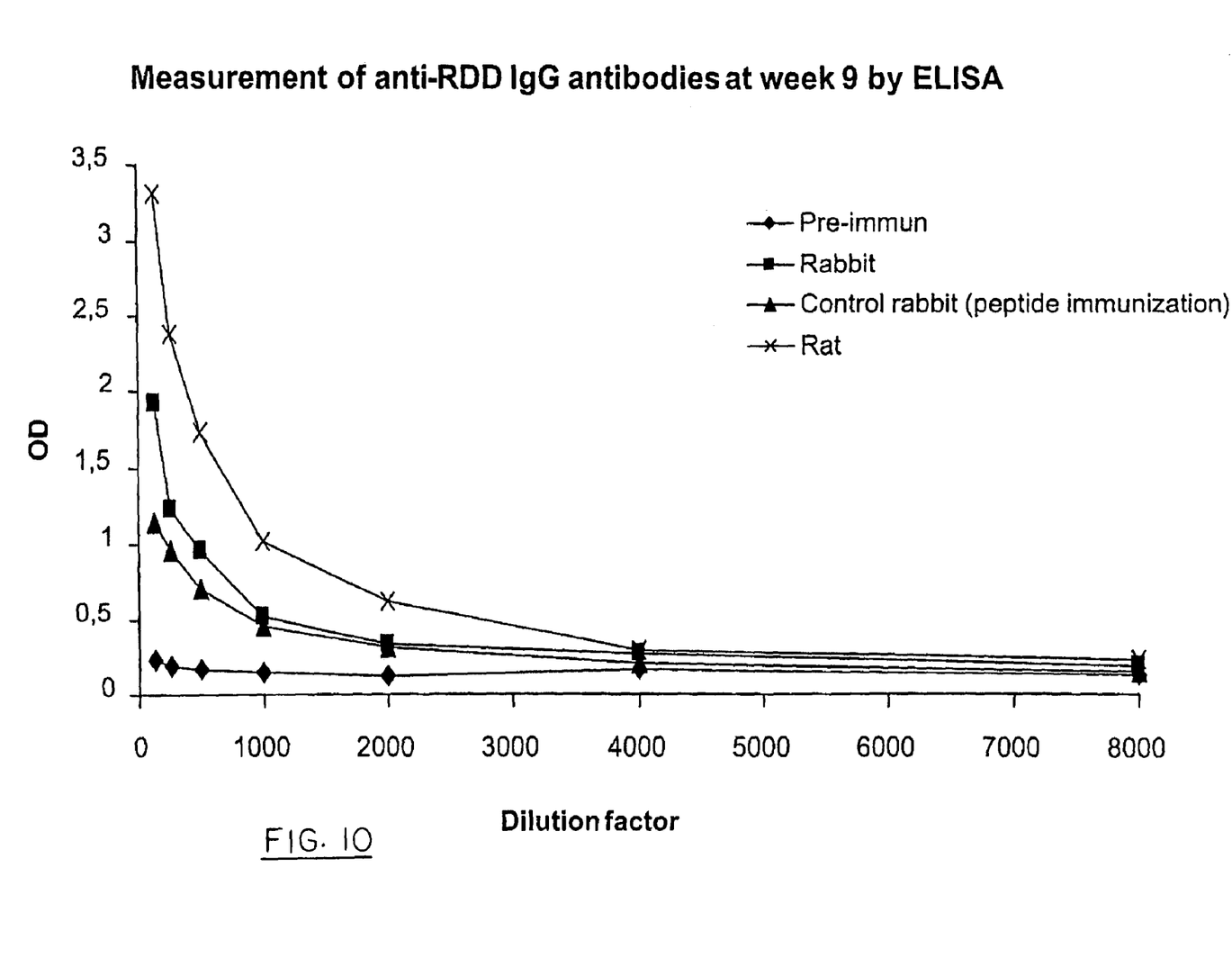
FIG. 10. Measurement of anti-RDD IgG antibodies produced in rabbit and rat.

As shown in FIG. 10, anti-RDD IgG antibodies were produced at week 9 after immunization of rabbits and rats by muscle electrotransfers. This immunization by electrotransfer induced an anti-RDD antibody production as efficient than a classical immunization by peptide injection to rabbits (see control rabbit curve). Same results were obtained for rats at week 16.

Furthermore, these polyclonal anti-RDD sera obtained in rabbits and rats were able to specifically detect recombinant RDD in western blot experiments.

REFERENCES BIBLIOGRAPHIQUES

AIHARA, H., and MIYAZAKI, J. (1998). Nat. Biotechnol. 16, 867-870.
ANDRE, F., and MIR, L. M. (2004). Gene Ther. 11 Suppl 1, S33-S42.
Ausubel, F. M. et al. (1994). *Current Protocols in Molecular Biology*. Wiley, New York.
BETTAN, M. et al. (2000). Mol. Ther. 2, 204-210.
BUREAU, M. F. et al. (2000). Biochim. Biophys. Acta 1474, 353-359.
GEHL, J., and MIR, L. M. (1999). Biochim. Biophys. Res. Commun. 261, 377-380.
GEHL, J., SKOVSGAARD, T., and MIR, L. M. (1998). Anticancer Drugs 9, 319-325.
GEHL, J. et al. (1999). Biochim. Biophys. Acta 1428, 233-240.
GLASS, L. F. et al. (1997). J. Am. Acad. Dermatol. 37, 596-599.
GOLZIO, M. et al. (2002). Proc. Natl. Acad. Sci. USA 99, 1292-1297.
HELLER, L. et al. (2000). Gene Ther. 7, 826-829.
HELLER, L. C., and COPPOLA, D. (2002). Gene Ther. 9, 1321-1325.
HELLER, R. et al. (1996). FEBS Left. 389, 225-228.
KLENCHIN, V. A. et al. (1991). Biophys. J. 60, 804-811.
MATSUMOTO, T. et al. (2001). Gene Ther. 8, 1174-1179.
MIKLAVCIC, D. et al. (2000). Biochim. Biophys. Acta 1523, 73-83.
MIR, L. M. et al. (1991a). C. R. Acad. Sci. III 313, 613-618.
MIR, L. M. et al. (1999). Proc. Natl. Acad. Sci. U.S.A 96, 4262-4267.
MIR, L. M. et al. (1998a). C. R. Acad. Sci. III 321, 893-899.
MIR, L. M. et al. (1998b). Br. J. Cancer 77, 2336-2342.
MIR, L. M. et al. (1991b). Eur. J. Cancer 27, 68-72.
MURAMATSU, T. et al. (1997). Biochem. Biophys. Res. Commun. 233, 45-49.
NEUMANN, E. et al. (1996). Biophys. J. 71, 868-877.
PODDEVIN, B. et al. (1991). Biochem. Pharmacol. 42 Suppl, S67-S75. et al.,
BARROSO, B. et al. (2002). Arch. Med. Res. 32, 273-276.
ROLS, M. P. et al. (1998). Nat. Biotechnol. 16, 168-171.
SATKAUSKAS, S. et al. (2001). Mol. Ther. 4, 317-323.
SATKAUSKAS, S. et al. (2002). Mol. Ther. 5, 133-140.
SERSA, G. et al. Z. (1998). Eur. J. Cancer 34, 1213-1218.
SOUBRIER, F. et al. (1999). Gene Ther. 6, 1482-1488.
SUKHAREV, S. I. et al. (1992). Biophys. J. 63, 1320-1327.
SUZUKI, T. et al. (1998). FEBS Lett. 425, 436-440.
TITOMIROV, A. V. et al. (1991). Biochim. Biophys. Acta 1088, 131-134.
TROCHON-JOSEPH, V. et al., Cancer Research 2004, 64:2062-2069.
WELLS, J. M. et al. (2000). Gene Ther. 7, 54-547.
ZAHAROFF, D. A. et al. (2002). Gene Ther. 9, 1286-1290.
ZAHAROFF, D. A., and YUAN, F. (2004). Bioelectrochemistry 62, 37-45.
ZHANG, L. et al. (1996). Biochem. Biophys. Res. Commun. 220, 633-636.

The invention claimed is:

1. A method for the electrically mediated gene transfer of a nucleic acid into muscular or tumoral cells of a Human or an animal, comprising bringing the nucleic acid into contact with the cells and electrically stimulating the cells in vivo by a process consisting of:
   directing at least one pulse of a High Voltage field strength of between 200 and 2000 volts/cm; followed by,
   a single pulse of Low Voltage field strength of between 50 and 200 volts/cm and of duration of between 300 and 2000 ms, to thereby transfer the gene into the cell.

2. The method according to claim 1, wherein the single pulse of Low Voltage has a field strength of between 50 and 140 volts/cm.

3. The method according to claim 1, wherein the single pulse of Low Voltage has a field strength of between 80 and 120 volts/cm.

4. The method according to claim 1, wherein the single pulse of Low Voltage has a field strength of between 90 and 110 volts/cm.

5. The method according to claim 1, wherein the single pulse of Low Voltage has a field strength of 100 volts/cm.

6. The method according to claim 1, wherein the High Voltage field strength of between 200 and 1400 volts/cm.

7. The method according to claim 6, wherein the High Voltage field strength of between 400 and 1200 volts/cm.

8. The method according to claim 6, wherein the High Voltage field strength of between 600 and 800 volts/cm.

9. The method according to claim 7, wherein the High Voltage field strength of 700 volts/cm.

10. The method according to claim 1, wherein the cells are muscle cells.

11. The method according to claim 1, wherein the single pulse of Low Voltage has a field strength of between 100 and 200 volts/cm.

12. The method according to claim 1, wherein the single pulse of Low Voltage has a field strength of between 120 and 160 volts/cm.

13. The method according to claim 1, wherein the single pulse of Low Voltage has a field strength of 140 volts/cm.

14. The method according to claim 1, wherein the High Voltage field strength of between 400 and 2000 volts/cm.

15. The method according to claim 14, wherein the High Voltage field strength of between 800 and 1600 volts/cm.

16. The method according to claim 14, wherein the High Voltage field strength of between 900 and 1200 volts/cm.

17. The method according to claim 14, wherein the High Voltage field strength of 1000 volts/cm.

18. The method according to claim 1, wherein the cells are tumoral cells.

19. The method according to claim 1, wherein the single pulse of Low Voltage has a duration of between 300 and 800 ms.

20. The method according to claim 19, wherein the single pulse of Low Voltage has a duration of between 350 and 600 ms.

21. The method according to claim 19, wherein the single pulse of Low Voltage has a duration of 400 ms.

22. The method according to claim 1, wherein the single pulse of Low Voltage has a polarity which is opposite to that of the High Voltage pulse.

23. The method according to claim 1, wherein a single High Voltage pulse is used.

24. The method according to claim 1, wherein the High Voltage field pulse(s) having a duration of between 10 and 1000 μs.

25. The method according to claim 24, wherein the High Voltage field pulse(s) having a duration of between 50 and 200 μs.

26. The method according to claim 25, wherein the High Voltage field pulse(s) having a duration of 100 μs.

27. The method according to claim 1, wherein High Voltage pulse and Low Voltage pulse are separated by a lag.

28. The method according to claim 27, wherein the lag is of between 300 ms and 3000 s.

29. The method according to claim 28, wherein the lag is of between 500 ms and 1000 s.

30. The method according to claim 29, wherein the lag is of 1000 ms.

31. The method according to claim 1, wherein the nucleic acid encodes the Recombinant human Desintegrin Domain of ADAM-15 protein.

32. The method of claim 1, wherein the nucleic acid comprises the sequence SEQ ID NO: 1.

33. The method of claim 1, wherein the nucleic acid encodes the Recombinant human Desintegrin Domain of ADAM-15 polypeptide whose sequence is SEQ ID NO: 2.

34. The method according to claim 1, wherein the nucleic acid encodes a Recombinant human Desintegrin Domain of ADAM-15 polypeptide or a fragment thereof that has the same activity as the whole Recombinant human Desintegrin Domain of ADAM-15 polypeptide.

35. The method according to claim 1, wherein the nucleic acid encodes an active molecule or several active molecules in the tissue cells.

36. The method according to claim 1, wherein the method mediates gene transfer of two or more nucleic acids, in which each nucleic acid encodes for a different active molecule in the tissue cells.

\* \* \* \* \*